United States Patent [19]

Stetler

[11] Patent Number: 5,340,720
[45] Date of Patent: Aug. 23, 1994

[54] METHODS OF DIAGNOSING AND MONITORING RHEUMATIC DISEASES

[75] Inventor: Dean A. Stetler, Lawrence, Kans.

[73] Assignee: University of Kansas, Lawrence, Kans.

[21] Appl. No.: 442,804

[22] Filed: Nov. 29, 1989

[51] Int. Cl.$^5$ ............... G01N 33/573; G01N 33/564
[52] U.S. Cl. ................... 435/7.4; 435/7.92; 435/7.94; 435/7.95; 436/506; 436/509; 436/518; 436/804; 436/811
[58] Field of Search ............. 435/7.1, 7.5, 7.9, 7.6, 435/7.92, 7.94, 7.95, 15, 975; 436/509, 518, 528, 529, 530, 531, 543, 547, 800, 804, 808, 811, 506

[56] References Cited

U.S. PATENT DOCUMENTS 4,582,793  4/1986  Jacob et al. ................ 435/7.92

OTHER PUBLICATIONS

Reimer et al, J. Clin. Invest., 79:65–72 (Jan. 1987).
Voller et al, "Enzyme-Linked Immunosorbent Assay" in Manual of Clinical Laboratory Immunology, Rose et al, eds., pp. 99–109 (1986).
Rose et al, Proc. Natl Acad. Sci. USA 78(5):2833–2837 (May 1981).
Morris et al, Autoimmunity, 2:241–251 (1989).
Buhler et al, J. Biol. Chem. 255(20):9949–9954 (1980).
Allison et al, Cell. 42:599–610 (Sep. 1985).
Stetler et al, Proc. Natl. Acad. Sci. USA 82:6797–6801 (Oct. 1985).
K. M. Rose, in RNA Polymerase and the Regulation of Transcription, pp. 427–430 (1986).
D. Stetler et al., J. Exp. Med, vol. 162, 1985, pp. 1760–1770.
Stetler and Cavallo, "Anti-RNA Polymerase Antibodies: Potential Role in the Induction and Progression of Murine Lupus Nephritis", J. Immunol. 138(7) pp. 2119–2123 (Apr. 1, 1987).
Coonrod, "Urine as an Antigen Reservoir for Diagnosis of Infectious Diseases." The American Journal of Medicine pp. 85–92 (Jul. 28, 1983).

Primary Examiner—Carol E. Bidwell
Attorney, Agent, or Firm—Wean K. Wong

[57] ABSTRACT

Assays which aid in diagnosing systemic lupus erythematosus and rheumatoid arthritis are disclosed. One assay tests urine samples for the presence or absence of an RNA polymerase I antibody which specifically binds with RNA polymerase I antigen and another assay tests for the presence or absence of an RNA polymerase I antigen that specifically binds with an antibody to RNA polymerase I.

8 Claims, No Drawings

METHODS OF DIAGNOSING AND MONITORING RHEUMATIC DISEASES

BACKGROUND OF THE INVENTION

1. Field of the Invention

The present invention relates generally to methods of diagnosing and monitoring rheumatic diseases. More particularly, the invention involves several related assays: an assay for the diagnosis of rheumatic disease, an assay for the differential diagnosis of rheumatic disease, an assay for determining the severity of the disease condition and an assay for determining the prognosis of a rheumatic disease.

2. Description of Related Art

Autoimmune diseases are defined as diseases which affect an individual in a manner to cause antibodies to be produced against constituents of the individual's own tissues. Autoimmune diseases may be classified into two broad categories: systemic and organ-specific diseases. The rheumatic diseases include a group of disorders which are within the systemic category. The group includes systemic lupus erythematosus (SLE), mixed connective tissue disease, rheumatoid arthritis (RA), Sjogren's syndrome, and scleroderma.

The cause of RA is unknown. Typically, a patient's clinical and pathological findings and disability are the result of chronic inflammation of synovial membranes. Spontaneous remissions and exacerbations are characteristic of the disease. SLE is a chronic, inflammatory disease of unknown cause which may affect the skin, joints, kidneys, nervous system, serous membranes and other organs. The classic clinical course of the disease is characterized by periods of remissions and relapses.

The systemic nature and relatively nonspecific symptoms of the diseases, particularly SLE and RA, often make the diseases difficult to diagnose and difficult to distinguish. An assay method which would enable the clinician to distinguish and discriminate between SLE and RA is highly desired.

Therapeutic agents such as prednisone, azathioprine, methotrexate and cyclophosphamide are used to treat SLE and other rheumatic diseases. These therapeutic agents, however, produce undesirable side effects and adverse reactions because they act by suppressing the immune system. Therefore, the dosages administered require careful control. In addition, it is possible to discontinue administration of the therapeutic agents when the disease goes into remission, which often happens with SLE, but at the first signs of relapse, the therapeutic agent must be readministered. Thus, there is also a need for a test which can be used to monitor the severity of rheumatic disease so that the dosages of such therapeutic agents can be adjusted, discontinued or resumed.

Traditionally, clinicians use a combination of tests and observations to determine the severity of SLE disease and to adjust drug therapy accordingly. For example, the Lupus Activity Criteria Count (LACC) as described by Urowitz, et al., *J. Rheumatol.*, 11,783 (1983) is frequently used. A LACC score of +2 or greater indicates "active" disease. The presence of each of the following is counted as +1:

1. arthritis;
2. abnormal blood tests: greater than 4000 white blood cells (WBC) per milliliter, CH50 (complement) values of less than 150, or anti-double-stranded DNA antibody titer of greater than 450;
3. new rash, hair loss or oral ulcers;
4. pericarditis;
5. central nervous system involvement: seizures or psychosis;
6. vasculitis; and
7. urine tests: greater than five red blood cells (RBC) per milliliter.

In addition, because glomerulonephritis is cased by SLE, tests of kidney function (such as those for proteinuria and blood urea nitrogen [BUN]) are also used to monitor the severity of disease.

Conventional diagnostic tests for rheumatic diseases, such as SLE, have been based upon the detection of autoantibodies to DNA or to nuclear antigens in the patient's blood. Some of these serum tests are described in the following patents.

U.S. Pat. No. 4,234,563 describes a method for detecting serum anti-DNA antibodies and serum antibodies to extractable nuclear antigens (ENA) in SLE patients. DNA-methylated bovine serum albumin conjugates or thymic extracts are used as capture antigens in such assays to detect serum anti-DNA or anti-ENA antibodies.

U.S. Pat. No. 3,897,212 describes a direct radioimmunoassay for detecting serum anti-DNA antibodies in SLE patients. The serum is incubated with radioactively labelled DNA, and anti-DNA antibodies are measured by determining the amount of radioactive label in the resulting precipitate.

U.S. Pat. No. 3,997,657 describes a method to detect anti-nuclear protein antibodies in serum using a dry slide technique. The method involves fixing thymus cell extract to a glass slide, incubating the serum sample on the slide and indirect immunofluorescent detection of bound antibodies.

U.S. Pat. No. 4,314,987 describes a method of diagnosing rheumatic diseases based upon patterns of fluorescent antinuclear antibodies, followed by testing for anti-DNA or anti-ENA antibodies. More specifically, the method allows for the interpretation of existing tests and is therefore limited by the accuracy of such tests.

U.S. Pat. No. 4,582,793 describes a method for the diagnosis of rheumatic diseases based upon the detection of serum antibodies specific for RNA polymerase I antigen, or its individual subunits.

Such methods require the use of the patient's serum as the test sample for the detection of antibodies. There is a need, therefore, for methods which detect antigens, as well as antibodies, that are characteristic of rheumatic diseases and which use body fluids which are obtainable through noninvasive as well as invasive techniques. The present invention is primarily directed to the detection of such antigens and antibodies in the patient's urine so that the assay can be performed without the need for the invasive collection of test samples.

SUMMARY OF THE INVENTION

The purpose of the present invention is to provide assays for the detection of RPI antigen and antibody which are related to rheumatic diseases. It is also the purpose of the present invention to interpret the results of such assays to enable the diagnosis of rheumatic disease, the differential diagnosis of RA and SLE, the determination of the severity of the rheumatic disease and the determination of disease prognosis.

One method for detecting rheumatic disease in a patient involves detecting an antibody in a urine sample, wherein the antibody is reactive with a RNA polymerase I.

Another method for detecting rheumatic disease involves detecting an antigen in a test sample, wherein the antigen is reactive with an antibody specific for RNA polymerase I.

The immediate future course of the disease can also be determined by comparing the results of the antigen and antibody assays. In one example of such comparative radioimmunoassays, if the resultant value of the antigen determination is significantly greater than that of the antibody determination, it is predicted that the patient's disease will decrease in severity. If the value of the antigen determination is significantly less than the value of the antibody determination, it is predicted that the patient's disease will increase in severity. If the relative quantities or assay values of the antigen and antibody determinations are substantially similar, it is predicted that the activity of the patient's disease will remain stable.

DETAILED DESCRIPTION OF THE INVENTION

The present invention provides novel methods for diagnosing and monitoring rheumatic diseases by detecting disease-related antigens and/or antibodies. While the following description focuses mainly upon SLE and RA, the invention can be directed generally to rheumatic diseases.

The methods of the present invention preferably involve the detection and/or measurement of RNA polymerase I antigens and antibodies in urine, although the antigens and antibodies may be detected in other body fluids. RNA polymerase I (RPI) is an enzyme composed of about eight or nine distinct polypeptide subunits ranging in molecular weight from 190,000 daltons to 17,000 daltons. The enzyme is localized in the nucleus of all eucaryotic cells. It is the enzyme responsible for transcribing ribosomal RNA genes localized in the nucleus. The enzyme is complex and contains many antigenic determinants or epitopes, some of which are shared by other proteins.

As used herein, "test sample" or "body fluid sample" typically refer to a naturally occurring or artificially formed liquid test medium suspected of containing the analyte of interest. The test sample is generally a biological fluid or a dilution thereof. Biological fluids from which an analyte can be determined include serum, whole blood, plasma, urine, saliva, amniotic and cerebrospinal fluids, and the like.

As described in detail in the examples hereinafter, assays were designed and performed wherein RPI antigen was detected in 38 of 91 urine samples from patients who had been previously diagnosed as having SLE based upon alternative diagnostic methods. The levels of antigen found were well above those levels found in healthy individuals. Of the 91 samples, 20 samples were from patients considered to have active SLE based upon the LACC scoring system. RPI antigens were detected in 18 of these 20 samples. In contrast, significant levels of RPI antigen were detected in only 2 of 23 urine samples from patients who had been previously diagnosed as having RA.

The high percentage of SLE patients, and particularly active SLE patients, who were found to have levels of RPI antigen that were significantly above those found in healthy individuals, illustrated the utility of detecting the RPI antigen for diagnosing rheumatic disease. In addition, it was discovered that the patient's disease status can be classified based upon the quantity of RPI antigen in the urine. Furthermore, the difference in the numbers of active SLE patients in comparison to RA patients who had elevated levels of RPI antigens also illustrated the advantageous use of the test in differentiating between the two diseases.

Before proceeding further with the description of various specific embodiments of the present invention, a number of terms will be defined. A variety of assay techniques in which the object of present invention can be achieved are also described.

The term "analyte" refers to either the RPI antigen or the anti-RPI antibody.

The term "test sample" typically refers to a urine sample, but the detection of analyte need not be limited thereto. Because the assays of the present invention are very sensitive, only small amounts of test sample are required. Any amount that is sufficient for the completion of the assay may be used. For example, the anti-RPI antibody assay can be performed with approximately 0.00003 milliliters of urine, and the RPI antigen assay can be performed with less than $1 \times 10^{-6}$ milliliters of urine.

The term "indicator reagent" refers to an assay reagent comprising a detectable label directly or indirectly attached to a specific binding member which is capable of directly or indirectly binding to the analyte to indicate the presence, absence or amount of the analyte. A variety of different indicator reagents can be formed by varying either the label or the specific binding member. In general, the indicator reagent is detected after it has formed a complex with either the analyte or a complementary specific binding member, but the unbound indicator reagent can also be detected.

The term "specific binding member" refers to a member of a specific binding pair, i.e., two different molecules wherein one of the molecules through chemical or physical means specifically binds to the second molecule. In addition to antigen and antibody specific binding pairs, other specific binding pairs include, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well-known to those skilled-in-the-art.

The term "label" refers to any substance which is attached to a specific binding member and which is capable of producing a signal that is detectable by visual or instrumental means. Various suitable labels for use in the present invention can include chromogens; catalysts; fluorescent compounds; chemiluminescent compounds; radioactive labels; direct visual labels including colloidal metallic and non-metallic particles, dye particles, enzymes or substrates, or organic polymer latex particles; liposomes or other vesicles containing signal producing substances; and the like.

A large number of enzymes suitable for use as labels are disclosed in U.S. Pat. No. 4,275,149, columns 19-23, herein incorporated by reference. In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

An especially preferred class of labels includes the visually detectable, colored particles which enable a direct colored readout of the presence or concentration, of the analyte in the sample without the need for using additional signal producing reagents. Materials for use as such particles include colloidal metals, such as gold, and dye particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed Jul. 9, 1987. Organic polymer latex particles for use as labels are disclosed in co-owned and copending U.S. patent application Ser. No. 248,858, filed Sept. 23, 1988.

The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "capture binding member" refers to a specific binding member which can directly or indirectly bind the analyte or indicator reagent and which is bound or is capable of being bound to a solid phase, or is capable of being precipitated, such that the capture binding member can be separated from the test sample and other assay reagents by any means.

The term "capture reagent" refers to a capture binding member which is directly or indirectly attached to a solid phase material to enable the separation of the capture binding member, and analyte or indicator reagent that is bound thereto, from unbound analyte and assay reagents. Typically, the attachment of the capture binding member to the solid phase material is substantially irreversible and can include covalent mechanisms. The capture reagent of the present invention, however, is not limited to a capture binding member bound to an insoluble solid phase material. In an agglutination assay, the capture binding member of the capture reagent can be bound to a soluble carrier material such as bovine serum albumin.

The term "solid phase material" refers to any suitable chromatographic, bibulous, porous or capillary material or other conventional solid material, well-known to those skilled-in-the-art, used to immobilize specific binding members. In the present invention, the solid phase material can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well-known to those skilled-in-the-art. The solid phase material can also include, without limitation, polyacrylamide beads, polystyrene beads or tubes, magnetic beads, a microtitre plate or a glass or plastic test tube.

Natural, synthetic or naturally occurring materials that are synthetically modified, can be used as a solid phase material including polysaccharides, e.g., cellulose materials such as paper and cellulose derivatives such as diazobenzyloxymethylcellulose, nitrocellulose, 2-aminophenylthioethercellulose, and cellulose acetate; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (e.g., cotton) and synthetic (e.g., nylon); porous gels such as silica gel, agarose, dextran, and gelatin; polymeric films such as polyacrylates; protein binding membranes; and the like. The solid phase material should have reasonable strength or strength can be provided by means of a support, and it should not interfere with the production of a detectable signal.

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles, associated with the solid phase base material, are not capable of substantial movement to positions elsewhere within that material. The microparticles can be selected by one skilled-in-the-art from any suitable type of particulate material including those composed of polystyrene, polymethylacrylate, polypropylene, polytetrafluoroethylene, polyacrylonitrile, polycarbonate or similar materials. The size of the microparticles is not critical, although it is preferred that the average diameter be smaller than the average pore size of the solid phase base material if such is used.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the indicator reagent is capable of binding the ancillary specific binding member which is in turn capable of binding the analyte.

It will be appreciated by those skilled-in-the-art that the selection of any given label, binding member, ancillary binding member or solid phase material is generally not critical to the present invention. The materials are chosen to optimize the results provided by the chosen assay configuration.

The object of present invention can be achieved by a variety of binding assay configurations and formats which enable the detection or measurement of RPI antigen and/or RPI antibody to diagnose, stage or predict the course of rheumatic disease. The RPI antigen and RPI antibody were found to be readily detectable in urine samples by means of binding assays which are generally categorized into one of two major classes, homogeneous and heterogeneous assays. These assays may be further divided into sandwich and competitive assay formats, and variations thereof.

In a solid phase sandwich assay, the capture reagent typically involves a specific binding member which has been bound to a solid phase material. For example, the specific binding member can be an immobilized antibody which will bind to an antigen-analyte in the test sample, or the specific binding member can be an immobilized antigen which will bind to an antibody-analyte in the test sample. The capture reagent is contacted to a test sample, suspected of containing the analyte, and to an indicator reagent comprising a second specific binding member that has been labeled, for example, a labeled anti-analyte antibody. The reagents can be mixed simultaneously or added sequentially, either singly or in combination. A binding reaction results in the formation of a capture reagent/analyte/indicator reagent complex immobilized upon the solid phase material. The assay can also comprise the step of separating the resultant complex from the excess reagents and test sample. The complex retained on the solid phase material is detected by examining the solid phase for the indicator reagent. If analyte is present in the sample, then label will be present on the solid phase material. The amount of label on the solid phase is a function of the amount of analyte in the sample.

The assays of the present invention can be carried out using any of the sandwich assay formats, including the forward, reverse and simultaneous techniques. Typically, a forward assay involves the contact of the test sample to the capture reagent followed by a certain incubation period which is in turn followed by the addition of the indicator reagent. A reverse assay involves the addition of the indicator reagent to the test sample followed by the addition of the capture reagent after a certain incubation period. A simultaneous assay involves a single incubation step as the capture reagent and indicator reagent are both contacted to the test sample at the same time.

In addition, the present invention can be used in an indirect sandwich assay with the formation of a complex of capture reagent/analyte/analyte-specific binding member/indicator reagent. In this case, the additional analyte-specific binding member is the ancillary specific binding member.

The methods of the present invention can also be carried out using competitive assay formats. In a solid phase competitive assay, the capture reagent again typically involves a specific binding member which has been affixed to a solid phase material and which is contacted with both test sample and an indicator reagent. The indicator reagent, however, can be formed from an analyte or analyte-analog which has been conjugated with a label. A binding reaction occurs and results in the formation of complexes of (1) immobilized capture reagent/analyte complex and (2) immobilized capture reagent/indicator reagent complex. Alternatively, the immobilized specific binding member can be an analyte or analyte-analog with which the test sample analyte competes for binding to the indicator reagent. In the competitive assay, the amount of label on the solid phase is inversely related to the amount of analyte in the sample. Thus, a positive test sample will generate a decrease in signal.

The homogeneous assay configurations do not require the separation of the test solution and the indicator reagent prior to the detection of the indicator reagent or binding complexes. This broad classification includes many formats such as agglutination and precipitation assays as well as others known to those skilled-in-the-art for the detection of analytes. Both direct and indirect agglutination assays can be performed.

In the present invention, a solid phase sandwich assay is preferably used to detect the presence or amount of anti-RPI antibodies in urine. Typically, the capture reagent is RPI antigen, or individual subunits thereof, immobilized upon a solid phase material. After the antigen is affixed to the solid phase material, the urine sample is incubated with the capture reagent for a period of time and under conditions sufficient for the formation of specific complexes between anti-RPI antibodies in the urine and the RPI antigen. The solid phase material can then be washed with a buffer solution to remove unbound test sample. The buffer solution can be any buffer conventionally known and used by those skilled-in-the-art. The resultant complexes are then incubated with an indicator reagent, such as a second labeled RPI antigen, for a period of time and under conditions sufficient for the formation of a ternary complex. The unreacted indicator reagent is then removed by again washing the solid phase with a buffer solution. The quantity of indicator reagent bound to the solid phase is then measured by a technique compatible with the label component of the indicator reagent. If quantitated, the amount of indicator reagent bound to the solid phase is proportional to the quantity of urinary anti-RPI antibody bound to the solid phase.

Another embodiment of the present invention involves the detection of RPI antigen. The methodology is similar to that for the detection of anti-RPI antibodies. RPI antigen from the test sample is immobilized upon the solid phase material either directly or through the use of anti-RPI antibodies which have been immobilized upon the solid phase material. An indicator reagent containing, for example, labeled anti-RPI antibodies is then incubated with the immobilized analyte for a period of time and under conditions sufficient for formation of a complex between the anti-RPI antibodies and the immobilized analyte. The amount of indicator reagent bound to the solid phase is proportional to the quantity of urinary RPI antigen bound to the solid phase.

It should be noted that the specific binding member of the capture reagent and indicator reagent in an assay can be identical or different. For example, while the capture reagent can be an anti-RPI antibody, antibody fragment, etc., used to immobilize the RPI antigen upon the solid phase, the indicator reagent can be any labeled binding member which will also bind to the antigen-analyte. Similarly in an assay to detect anti-RPI antibody, while the capture reagent can be any RPI antigen related member, including but not limited to RPI, subunits of RPI, polypeptides immunologically related to RPI, and synthetic or genetically engineered polypeptides containing RPI-related epitopes, the indicator reagent can be any labeled binding member which will also bind to the analyte. Such specific binding members include, but are not limited to, protein A (such as that obtained from Staphylococcus), protein G (such as that obtained from Streptococcus), as well as antibodies directed against IgG of the species in which the anti-RPI antibodies are produced.

By observing the results of RPI antigen and/or anti-RPI antibody assays, an accurate diagnosis or differentiation between rheumatic diseases, such as SLE and RA, and non-rheumatic diseases can be made, a determination of the severity of the disease is made possible, and a comparison of the results of the two assays provides a means to predict the immediate future course of the disease. In the present invention, the results of the assays used to detect RPI antigens and antibodies are interpreted as described below.

A. Test results for assays detecting the presence or amount of RPI antigen in a test sample A negative assay result, i.e., a normal level of RPI antigen is found, is interpreted as follows:
1. If the patient has not been previously diagnosed as having a rheumatic disease, a negative test result also indicates that the patient does not have rheumatic disease.
2. If the patient has been previously diagnosed as having an active rheumatic disease, and the question is whether the disease is SLE or RA, a negative test result indicates that the patient has RA and not SLE.
3. If the patient has been previously diagnosed as having SLE, a negative test result indicates that the disease is currently inactive.

A positive assay result, i.e., an elevated level of RPI antigen is found, is interpreted as follows:
1. If the patient has not been previously diagnosed as having a rheumatic disease, a positive test result indicates that the patient does have a rheumatic disease, and suggests that the patient has SLE.
2. If the patient has been previously diagnosed as having an active rheumatic disease, and the question is whether the disease is SLE or RA, a positive test result indicates that the patient has SLE and not RA.
3. If the patient has been previously diagnosed as having SLE, a positive test result indicates that the disease is active. The degree of elevation in RPI antigen level, as compared to a control value, is proportional to the degree of disease activity, i.e., the higher the antigen level, the more severe the disease state.

B. Test results for assays detecting the presence or amount of anti-RPI antibody in a test sample A negative assay result, i.e., a normal level of urine anti-RPI antibody is found, is interpreted as follows:
1. If the patient has not been previously diagnosed as having a rheumatic disease, a negative test result indicates that the patient does not have a rheumatic disease.
2. If the patient has been previously diagnosed as having an active rheumatic disease, and the question is whether the disease is SLE or RA, a negative test result indicates that the patient has RA and not SLE.

A positive assay result, i.e., an elevated level of urine anti-RPI antibody is found, is interpreted as follows:
1. If the patient has not been previously diagnosed as having a rheumatic disease, a positive test result indicates that the patient does have a rheumatic disease, and suggests that the patient has SLE.
2. If the patient has been previously diagnosed as having an active rheumatic disease, and the question is whether the disease is SLE or RA, a positive test result indicates that the patient has SLE and not RA.

C. Combined results of assays for RPI antigen and anti-RPI antibody

If a patient has been previously determined to have a rheumatic disease such as SLE, the values resulting from the assays for RPI antigen and anti-RPI antibody are compared. For example, in a radioimmunoassay format, the values resulting from assays for the determination of urinary RPI antigen and anti-RPI antibody can be compared and interpreted as follows:
1. If the value of the RPI antigen determination is significantly greater (e.g., more than about 1000 counts per minute [cpm] greater) than the value of the anti-RPI antibody determination, it is predicted that the patient's disease will decrease in severity.
2. If the value of the RPI antigen determination is substantially similar to the value of the anti-RPI antibody determination (e.g., values which are within about 1000 cpm of the value of the anti-RPI antibody determination), it is predicted that the activity of the patient's disease will remain stable.
3. If the value of the RPI antigen determination is significantly less (e.g., more than about 1000 cpm less than the value of the anti-RPI antibody determination), it is predicted that the patient's disease will increase in activity.

The values of 1000 cpm, as described above and in the specific examples which follow, are based upon a radioimmunoassay format using urine test samples diluted 1/10,000 for the antigen assay and 1/10 for the antibody assay. Thus, these assay results are not directly comparable in terms of quantity of antigen or antibody in a given volume of test sample. It will be understood by those skilled-in-the-art that an alteration in the procedure of one of the comparative assays would result in the necessity to restandardize the significance of the relative quantities or relative values of the two assays with respect to the future course of disease. For example, a change in the test sample source, dilution factors, assay reagents or assay format (such as an enzyme immunoassay) can lead to the need to reevaluate that which should be considered as a significantly greater or significantly lower assay value.

Thus, the assay methods of the present invention can be used both qualitatively and quanlitatively and are useful for the diagnosis of rheumatic disease, the differentiation between rheumatic diseases, the determination of disease severity and patient prognosis. Furthermore, the assays of the present invention provide an advantage over tests for anti-DNA antibodies in blood serum because anti-DNA antibodies are also found in individuals who have no history of rheumatic disease. Because the present invention can also be used to monitor the course of rheumatic disease it is of further utility in determining appropriate drug therapy dosages: a comparison of the values obtained from the RPI antigen assay and anti-RPI antibody assay can be used to predict the immediate future course of rheumatic disease, thereby enabling the adjustment of drug dosage in anticipation of an increase or decrease in disease activity.

The anti-RPI antibodies used in assay reagents in the following assay examples were generally produced by immunizing rabbits with purified RPI enzyme. The anti-RPI antibodies can also be raised by using RPI antigen to immunize other mammals, such as sheep, guinea pigs and mice; and fowl such as chickens, ducks and geese. An example of one conventional technique for the production of antibodies in rabbits is described by Rose, et al., *Proc. Nat. Acad. Sci. U.S.A.*, 78, 2833 (1981), which is incorporated by reference herein. In addition, hybridomas which produce anti-RPI antibodies can be prepared by fusing plasmacytoma cells of the appropriate species with lymphocytes from animals or humans which have initiated or have been induced to initiate, by in vitro or in vivo stimulation techniques, the production of antibodies directed against the RPI enzyme. As described above, the source of antibody is not critical, and the antibody can be a monoclonal or polyclonal antibody, a recombinant protein or antibody, a mixture(s) or fragment(s) thereof, as well as a mixture of an antibody and other specific binding members, so long as the binding member provides a functioning epitope for the recognition and binding of RPI antigen in the test sample.

RPI enzyme is present in all eucaryotic cells. Consequently, the enzyme is available from many sources for use as an antigen in the present invention. One source of purified RPI is a rat tumor, Morris hepatoma 3924A (University of Kansas, Lawrence, Kans.). The preparation of RPI from the Morris hepatoma is described in Rose, et al., *J. Bio. Chem.*, 256, 7468 (1981); Rose, et al., *Proc. Natl. Acad. Sci. U.S.A.* 78, 2833 (1981) and U.S. Pat. No. 4,582,793, which are incorporated by reference herein. Alternative sources of the RPI enzyme include other vertebrates and nonvertebrates, organs, tumors, organ culture or derived cell lines, or genetic chimeras containing the gene coding for individual RPI enzyme subunits. In addition, it is possible to utilize genetically engineered or synthetically produced peptides containing RPI antigenic determinants. Any source of the antigen is permissible, so long as the source provides a functioning epitope for the recognition and binding of anti-RPI antibody in the test sample. Furthermore, while RPI antigen or one of its individual subunits is preferred, any antigen or polypeptide immunologically related to RPI may be used; for example, protein kinase NII, RNA polymerase II or III, Sm antigen or anti-DNA antibodies.

The exemplary assays of the present invention typically involve the addition and incubation of several different reagents. A variety of different buffer and washing solutions can be used to stabilize the reagents and to remove excess reagents or test sample from the reaction. As is well-known to those skilled-in-the-art, modifications can be made in the buffer and washing solutions, as well as in the reaction times.

The assay reagents can also be provided in kit form. A test kit to detect anti-RPI antibody would typically contain a solid phase material upon which RPI antigen is immobilized and optionally include an appropriate supply of a suitable indicator reagent, buffers and washing solutions. A test kit to detect RPI antigen would typically contain a solid phase material upon which anti-RPI antibody is immobilized or upon which components of the patient's test sample can be immobilized (e.g., direct immobilization of the antigen upon the solid phase), and optionally include appropriate amounts of a suitable indicator reagent, buffers and washing solutions. Other components such as stabilizers and preservative agents can also be present in the kit and/or in the reagents.

The following examples describe, in detail, preferred assays according to the present invention. The examples are provided to further illustrate the advantages of the present invention and the specific experiments performed.

EXAMPLE 1

Assay for the Detection of Anti-RPI Antibodies a. Immobilization of RPI antigen on a solid phase RPI, from Morris hepatoma 3924A or other source, was diluted with Buffer I [containing 25 mM potassium phosphate (pH 7.5), 150 mM NaCl, 0.01% (w/v) sodium azide, and 0.1 mM phenylmethylsulfonylfluoride] to a concentration of 0.01 milligrams/milliliter. One microgram of the diluted enzyme was placed into each of a series of 400 microliter-capacity, flat-bottom, polystyrene wells (Immulon I, Dynatech Laboratories, Inc., Alexandria, Va.) and incubated at 37° C. for three hours. The enzyme solution was removed, and the wells were washed four times with Buffer I (0.1 mL each time). Buffer I, further containing one percent (w/v) bovine serum albumin as a blocking agent, was placed into each well, was incubated for one hour at room temperature, and was then removed.

b. Assay for anti-RPI antibody

Human urine (0.1 mL), diluted 1/10 in Buffer II [containing 50 mM Tris-HCl (pH 7.4), 150 mM NaCl, 5 mM EDTA, 0.05 percent (v/v) Nonidet P-40, and 0.1 mM phenylmethylsulfonylfluoride] was added to each well. The test sample was incubated for one hour at room temperature and for 16 hours at 4° C. The urine sample was removed, and the wells were washed four times (0.1 mL each time) with Buffer II. Buffer II (0.1 mL) containing radioactively-labeled ($^{125}$I) protein A (30–50 mCi/mg; $2 \times 10$–4 mCi/mL), as the indicator reagent, was added to each well and incubated for two hours at room temperature. The radioactive solution was removed, and the wells were washed four times (0.1 mL each time) with Buffer III [50 mM Tris-HCl (pH 7.4), 1M NaCl, 0.4% (w/v) N-laurylsarcosine, and 0.1 mM phenylmethylsulfonylfluoride]. Indicator reagent immobilized in the wells was then quantitated in a gamma counter. The amount of radioactivity remaining in the wells was proportional to the amount of antibody present in the test sample.

EXAMPLE 2

Detection of RPI Antigen a. Immobilization of RPI antigen on a solid phase

A urine sample was diluted 1/10,000 with Buffer I. The diluted sample (0.10 mL) was placed into each of a series of 400 microliter-capacity, flat-bottom, polystyrene wells (Immulon I) and incubated at 37° C. for three hours. The urine solution was then removed, and the wells were washed four times with Buffer I (0.10 mL each time). Buffer I (0.15 mL), further containing one percent (w/v) bovine serum albumin as a blocking agent, was placed into each well, was incubated for one hour at room temperature, and was then removed.

b. Assay for RPI antigen

Rabbit anti-RPI antibody (0.1 mL) diluted 1/100 in Buffer II, containing one percent bovine serum albumin, was added to each well and incubated for one hour at room temperature and for 16 hours at 4° C. The unbound antibody solution was removed, and the wells were washed four times (0.1 mL each time) with Buffer II. Indicator reagent, as described in Example 1, was added to each well and was incubated for two hours at room temperature. The radioactive solution was removed, and the wells were washed four times (0.1 mL each time) with Buffer III. The amount of radioactive indicator reagent remaining in each well was then measured in a gamma counter. The remaining radioactivity was directly proportional to the amount of antigen immobilized from the test sample.

EXAMPLE 3

The Relationship Between RPI Antigen and Disease Activity

RPI antigen was detected using assays according to the present invention, in a number of test samples, which were performed substantially in accordance with the procedures described in Example 2, above. Assays were performed wherein RPI antigen was detected in 38 of 91 urine samples from patients who had been previously diagnosed as having SLE based upon alternative diagnostic methods. The levels of detected antigen were higher than the antigen levels found in 43 healthy individuals. Of the 91 urine samples, 20 samples were from patients considered to have active SLE based upon the LACC scoring system. RPI antigens were detected in 18 of these 20 urine samples. In contrast, significant levels of RPI antigen were detected in only 2 of 23 urine samples from RA patients.

Tables 1 and 2, respectively, illustrate the resultant test data which demonstrated the relationship between the presence of RPI antigens in the urine of SLE patients and the ability to both determine disease activity and predict disease state. Each SLE patient was classified as having either inactive (I), mild (Mi), moderate (Mo) or severe (S) disease. A patient's disease was classified as inactive if the urine RPI antigen level was less than 750 cpm, mild if the urine RPI antigen level was between 750 cpm and 1200 cpm, moderate if the urine RPI antigen level was between 1200 cpm and 4000 cpm, or severe if the urine RPI antigen level was greater than 4000 cpm. The percentage of patients having a LACC score of 2 or greater (considered to be active SLE) was found to increase with increasing quantities of RPI antigen. Thus, the results demonstrated that the quantity of RPI antigen detected was related to SLE disease activity.

In the following tables, the number of patients in each classification group is represented by "n". "Percent of Patients LACC 2" refers to the percentage of patients, in each classification group, having a LACC score of at least 2, i.e., the percentage of patients considered to have active disease based upon the LACC scoring system. "Percent of Patients LACC less than 2" refers to the percentage of patients, in each classification group, having a LACC score of less than 2, i.e., the percentage of patients considered to have inactive disease based upon the LACC scoring system.

TABLE 1

Relationship Between the Quantity of RPI Antigen and SLE Disease Activity

| Classification based upon RPI in Urine | n | Percent of Patients LACC 2 |
| --- | --- | --- |
| I | 52 | 3.8 |
| I + Mi | 62 | 6.5 |
| Mi | 10 | 20.0 |
| Mi + Mo + S | 36 | 50.0 |
| Mo | 20 | 60.0 |
| Mo + S | 26 | 61.5 |

TABLE 1-continued

Relationship Between the Quantity of RPI Antigen and SLE Disease Activity

| Classification based upon RPI in Urine | n | Percent of Patients LACC 2 |
| --- | --- | --- |
| S | 6 | 66.7 |

The correlation between disease classification, based upon the RPI antigen assay, and the number of patients in each group who were considered to have active disease, based upon the LACC scoring system, indicated that the presence or quantity of RPI antigen detected was clearly related to SLE disease activity. Therefore, the results indicated the utility of the RPI antigen assay for monitoring SLE disease activity over time by performing the assay at regular intervals.

Due to the complexity of the rheumatic disease process and the nonspecific nature of the related clinical symptoms, a single conventional laboratory test will not reliably monitor rheumatic disease activity. For example, a number of tests and observations are used to generate values such as the LACC score. In accordance with the present invention, the results of RPI antigen assays were compared with the results of conventional laboratory tests to determine the RPI antigen assay's agreement with the LACC score. These data are shown in Table 2.

The incidence of "false positive" results with the RPI antigen assay was 38.5 percent. The LACC score, which is used for comparison purposes, is not always accurate, and this inaccuracy could account for the relatively high incidence of false positives. Nevertheless, the false positive rate for the RPI antigen assay was comparable to or significantly better than that of the seven conventional laboratory tests. When LACC scoring was not used, six of the seven conventional tests have false positive rates of 50 percent or greater. Therefore, the RPI antigen assay was more accurate.

Regarding "false negatives", the RPI antigen assay was also more accurate. The incidence of false negatives was 6.5 percent. The anti-dsDNA, BUN, creatinine, urine WBC and urine RBC tests produced between two and three times more false negatives with respect to active rheumatic disease than did the RPI antigen assay.

TABLE 2

Comparison of the Accuracy of RPI Assays in Prediciting Disease Status with the Accuracy of Commonly Used Laboratory Tests

| Test | n | Percent of Patients LACC 2 (active disease) | Percent of Patients LACC less than 2 (inactive disease) |
| --- | --- | --- | --- |
| Positive Result: | | True Positive | False Positive |
| Urine RPI (Mo + S) | 26 | 61.5 | 38.5 |
| Anti-dsDNA | 18 | 55.5 (50.0)* | 44.5 (50.0)* |
| CH50 | 32 | 56.3 (34.4)* | 43.7 (65.6)* |
| BUN | 5 | 40.0 | 60.0 |
| Creatinine | 8 | 62.5 | 37.5 |
| Urine Protein | 32 | 50.0 | 50.0 |
| Urine WBC | 23 | 43.5 | 56.5 |
| Urine RBC | 8 | 62.5 (25.0)* | 37.5 (75.0)* |
| Negative Result: | | False Negative | True Negative |
| Urine RPI (I + Mi) | 62 | 6.5 | 93.5 |
| Anti-dsDNA | 69 | 14.5 | 85.5 |
| CH50 | 56 | 5.7 | 94.3 |
| BUN | 79 | 20.3 | 79.7 |
| Creatinine | 79 | 17.7 | 82.3 |
| Urine Protein | 52 | 5.8 | 94.2 |
| Urine WBC | 61 | 13.1 | 86.9 |

TABLE 2-continued

Comparison of the Accuracy of RPI Assays in Prediciting Disease Status with the Accuracy of Commonly Used Laboratory Tests

| Test | n | Percent of Patients LACC 2 (active disease) | Percent of Patients LACC less than 2 (inactive disease) |
|---|---|---|---|
| Urine RBC | 76 | 13.2 | 86.8 |

*Because three of the laboratory tests were used in determining the LACC score, there may be an apparent correlation between a particular test and LACC score due to the fact that a point is added to the LACC score when such a test is positive. The numbers in parentheses represent the values obtained when the particular laboratory test is not considered in the LACC score. Because the RPI antigen assay result is not used int he LACC score, these latter values should be considered when com paring the results of tests used in the LACC score to the RPI antigen assay results.

EXAMPLE 4

The Prognosis of Rheumatic Disease

According to the present invention, anti-RPI antibody and RPI antigen assays using urine samples from SLE patients, RA patients and healthy controls were performed substantially in accordance with the procedures described in Examples 1 and 2, above. The resultant data further illustrated the advantageous use of assays of the present invention for the detection or measurement of RPI antigen and anti-RPI antibody and in diagnosing rheumatic disease, distinguishing between SLE and RA, determining the severity of disease and predicting the immediate future course of the disease.

When the test results of the anti-RPI antibody assays are compared with the test results of the RPI antigen assays, the combined data enabled the diagnosis of SLE and the differentiation between SLE and RA. Of 91 urine samples from SLE patients, 51 contained either RPI antigen or anti-RPI antibody, and 32 contained both. Of the 20 urine samples from active SLE patients (as determined by a LACC score of 2 or greater), 19 contained either the antigen or the antibody, and 18 contained both. In contrast, only 6 of the 23 urine samples from RA patients contained either the antigen or the antibody and none contained both. None of the urine samples from 43 healthy individuals contained either the antigen or the antibody.

To further illustrate the present invention, a comparison of the anti-RPI antibody assay value with the RPI antigen assay value was used to predict the immediate future course of the disease process. If the anti-RPI antibody test value was higher than the RPI antigen test value, it was predicted that the patient's disease would increase in severity. Conversely, if the value of the antibody determination was less than the value of the antigen determination, it was predicted that the patient's condition would improve. If the antigen and antibody test values were similar, it was predicted that the disease would remain at its current level of activity. Thirty five cases were studied. In 26 of these 35 cases, the prediction was correct. In seven of the nine cases in which the prediction was incorrect, the disease status did not change in a direction opposite to that predicted. Rather, in these cases, the disease status remained the same. In the remaining two cases, the disease status appeared to improve rather than worsen as predicted. It should be noted that the individuals in the case study were receiving therapeutic agents which could have influenced the course of the disease. None of the conditions of the patients worsened when it was predicted that they would improve. When there was a significant increase in disease activity as reported in eight of the cases, the predictions were accurate. Therefore, in accordance with the present invention, the experimental results indicated that the relative quantities or levels of anti-RPI antibodies and RPI antigens in the patient's urine were advantageously used to indicate the immediate future course of the rheumatic disease.

As described above the concepts of the present invention are applicable to various types of assays for detecting RPI antigen or anti-RPI antibody, and it will be appreciated that one skilled-in-the-art can conceive of many different assays to which the present inventive concepts can be applied. Accordingly, the embodiments described and the alternative embodiments presented herein are intended as examples rather than as limitations, and thus, the foregoing description of the invention is not intended to limit the invention to the particular embodiments disclosed, but encompasses all equivalents and subject matter within the spirit and scope of the invention as previously described and as set forth in the following claims.

What is claimed is:

1. A method which aids in diagnosing systemic lupus erythematosus or rheumatoid arthritis in a patient, comprising the steps of:
  (a) obtaining a sample of urine from the patient;
  (b) detecting an RNA polymerase I antibody in said sample, wherein said antibody specifically binds with RNA polymerase I and
  (c) correlating the presence or absence of the antibody with either rheumatoid arthritis or systemic lupus erythematosus, wherein if
  (1) said patient has not previously been diagnosed as having systemic lupus erythematosus or rheumatoid arthritis, then the presence of said antibody indicates that the patient has systemic lupus erythematosus;
  (2) said patient has not been diagnosed as having systemic lupus erythematosus or rheumatoid arthritis, then the absence of said antibody indicates that the patient does not have systemic lupus erythematosus or rheumatoid arthritis;
  (3) said patient has previously been diagnosed as having an undifferentiated rheumatoid disease selected from the group consisting of systemic lupus erythematosus and rheumatoid arthritis, then the presence of said antibody indicates said rheumatoid disease is systemic lupus erythematosus; and
  (4) said patient has previously been diagnosed as having an undifferentiated rheumatoid disease selected from the group consisting of systemic lupus erythematosus and rheumatoid arthritis, then the absence of said antibody indicates said rheumatoid disease is rheumatoid arthritis.

2. A method which aids in diagnosing systemic lupus erythematosus or rheumatoid arthritis, comprising the steps of:
  (a) obtaining a sample of urine from a patient;
  (b) detecting an RNA polymerase I antigen in said sample, wherein said antigen specifically binds with an antibody to RNA polymerase I; and
  (c) correlating the presence or absence of the antigen with either systemic lupus erythematosus or rheumatoid arthritis, wherein if
  (1) said patient has not previously been diagnosed as having systemic lupus erythematosus or rheumatoid arthritis, then the absence of said antigen indicates that the patient does not have systemic lupus erythematosus or rheumatoid arthritis;

(2) said patient has not previously been diagnosed as having systemic lupus erythematosus or rheumatoid arthritis, then the presence of said antigen indicates that the patient has systemic lupus erythematosus;

(3) said patient has previously been diagnosed as having an undifferentiated rheumatoid disease selected from the group consisting of systemic lupus erythematosus and rheumatoid arthritis, then the absence of said antigen indicates said rheumatoid disease is rheumatoid arthritis;

(4) said patient has previously been diagnosed as having an undifferentiated rheumatoid disease selected from the group consisting of systemic lupus erythematosus and rheumatoid arthritis, then the presence of said antigen indicates said rheumatoid disease is systemic lupus erythematosus; and (5) said patient has previously been diagnosed as having systemic lupus erythematosus, then the absence of said antigen indicates said systemic lupus erythematosus in currently inactive.

3. The method according to claim 2, comprising the steps of:
   (a) reacting said sample with a capture reagent, wherein said capture reagent comprises said antibody attached to a solid phase material, thereby forming a capture reagent/antigen complex;
   (b) reacting said complex with an indicator reagent comprises a label conjugated to a binding member specific for said antigen, thereby forming a ternary complex; and
   (c) determining the presence or amount of said indicator reagent on said solid phase.

4. The method according to claim 2, wherein said antigen is directly or indirectly immobilized upon a solid phase material, and wherein said antibody is a labeled antibody that specifically binds to said antigen,. thereby forming a detectable antigen/antibody complex on said sold phase.

5. A method of detecting anti-RNA polymerase I antibody in a urine sample from a patient comprising the steps of:
   (a) obtaining a sample of urine from said patient;
   (b) reacting said sample with RNA polymerase for a time and under conditions sufficient for said antibody to specifically bind to said RNA polymerase I, thereby forming a complex; and
   (c) detecting the presence or absence of said complex as an indication of the presence or absence of said antibody in said sample.

6. A method of detecting anti-RNA polymerase I antibody in a urine sample from a patient comprising the steps of:
   (a) reacting said urine sample with RNA polymerase I attached to a solid phase, for a time and under conditions sufficient for said antibody in said urine sample to specifically bind to said RNA polymerase I forming a complex on said solid phase;
   (b) reacting said complex with an indicator reagent, wherein said indicator reagent comprises a binding member which is specific for a human antibody and conjugated to a detectable label, for a time and under conditions sufficient to form a labeled ternary complex on said solid support; and
   (c) detecting the presence or absence of said labeled ternary complex as an indication of the presence or absence of said antibody in said urine sample.

7. A method of detecting RNA polymerase I antigen in a urine sample from a patient comprising the steps of:
   (a) obtaining a urine sample from said patient;
   (b) reacting said urine sample with an anti-RNA polymerase I antibody for a time and under conditions sufficient for said antigen in said urine sample to bind to said RNA polymerase I antibody forming an antigen-antibody complex; and
   (c) detecting the presence or absence of said complex as an indication of the presence or absence of said RNA polymerase I antigen in said urine sample.

8. A method of detecting RNA polymerase I antigen in a urine sample from a patient comprising the steps of:
   (a) obtaining a urine sample from said patient;
   (b) reacting said sample with anti-RNA polymerase I antibody attached to a solid support for a time and under conditions sufficient to form an antibody-antigen complex on said support;
   (c) reacting said complex with an indicator reagent, said indicator reagent comprising a binding pair member specific for said antigen conjugated to a detectable label for a time and under conditions sufficient to form a ternary complex on said support; and
   (d) detecting the presence or absence of said detectable label as an indication of the presence or absence of said antigen in said urine sample.

* * * * *